United States Patent [19]

McGlothlin et al.

[11] Patent Number: 4,855,169

[45] Date of Patent: Aug. 8, 1989

[54] PROPHYLACTIC SHEATH WITH AUGMENTED BORDER

[75] Inventors: Mark W. McGlothlin; Alice A. DePaul, both of San Diego, Calif.

[73] Assignee: Apex Medical Technologies, Inc., San Diego, Calif.

[21] Appl. No.: 148,750

[22] Filed: Jan. 27, 1988

[51] Int. Cl.$^4$ ............................................... B27N 5/02
[52] U.S. Cl. ..................................... 428/35.2; 428/57; 428/212; 428/220; 428/423.3; 428/423.9; 428/424.2; 428/424.6; 428/424.1; 428/447; 428/216; 128/842; 128/844
[58] Field of Search ...................... 428/35, 36, 57, 212, 428/213, 220, 423.3, 423.9, 447, 424.2, 424.6, 424.8, 216, 34.1, 34.3, 34.6, 34.7, 35.2, 35.7, 36.5, 36.8, 36.9, 36.91; 128/132 R, 138 R, 844, 842; 604/349

[56] References Cited

U.S. PATENT DOCUMENTS

| | | | |
|---|---|---|---|
| 2,567,926 | 9/1951 | Dunkelberger | 128/132 R |
| 2,670,736 | 3/1954 | Dunkelberger | 128/132 R |
| 2,904,041 | 9/1959 | Brown | 128/132 |
| 3,018,484 | 1/1962 | Koehn | 2/21 |
| 3,085,570 | 4/1963 | Penska | 128/132 |
| 3,282,414 | 11/1966 | Penska | 206/63.2 |
| 3,553,308 | 1/1971 | Kobayashi | 264/305 |
| 3,563,244 | 2/1971 | Asaka | 128/294 |
| 3,707,005 | 12/1972 | Giambrone | 2/163 |
| 3,992,766 | 11/1976 | Field | 29/235 |
| 4,095,293 | 6/1978 | Heavner | 2/168 |
| 4,100,309 | 7/1978 | Micklus | 427/2 |
| 4,354,494 | 10/1982 | Hogin | 128/294 |
| 4,576,156 | 3/1986 | Dyck et al. | 264/320 |
| 4,684,490 | 8/1987 | Taller et al. | 264/301 |
| 4,735,621 | 4/1988 | Heusel | 128/132 R |

FOREIGN PATENT DOCUMENTS 0147072 11/1984 European Pat. Off. .
31012 9/1971 Japan .

*Primary Examiner*—Ellis P. Robinson
*Assistant Examiner*—P. J. Ryan
*Attorney, Agent, or Firm*—Townsend and Townsend

[57] ABSTRACT

Thin-walled, high-strength prophylactic sheaths fabricated from elastomeric polymer materials are augmented along the border at the open end with a resilient material having a 100% tensile modulus substantially lower, preferably lower by at least about 75%, than that of the sheath material. This facilitates the rolling of the edge and stretching of the sheaths for purposes of application without compromising the high degree of sensitivity in terms of heat and sensation transmission associated with the thin-walled sheaths themselves.

23 Claims, No Drawings

PROPHYLACTIC SHEATH WITH AUGMENTED BORDER

BACKGROUND OF THE INVENTION

This invention relates to elastic prophylactic sheaths, such as those used as gloves, condoms, finger cots and the like. In particular, this invention relates to elastomeric polymer sheaths and the augmented borders at the open ends of these sheaths, which facilitate the placement of the sheaths over the body members on which they are used as well as their removal after use.

The use of prophylactic sheaths is continually broadening in both clinical and consumer applications. The sheath most commonly known to the consumer is the condom, with world-wide use in a wide range of civilizations and cultures, for both contraception and prevention of the transmission of sexually transmitted disease. The most common material form which condoms and other prophylactic sheaths are fabricated is latex.

Certain classes of elastomeric polymers offer advantages over latex as materials for prophylactic sheaths. Polyurethane, for example, has both a strength and a tensile modulus approximately three times those of latex. Similar properties are found in other thermoplastic elastomers, particularly block copolymers formed by combining hard and soft segments of appropriate structure in proportions and arrangements selected to provide the resulting copolymer with the desired properties. The selection of the particular segments as well as their proportions and arrangements in the block copolymer are within the knowledge of those skilled in the copolymer art.

The advantage of the use of such materials is that they can be used to form sheaths of less than half the thickness of the latex products but with equivalent strength. With such a reduced thickness, these products provide greater transmission of heat and sensation.

Specific classes of elastomeric polymers offer further advantages due to their chemical structure. Polyurethanes, for example, tend to soften in a warm, moist environment. They are also easier to sterilize and more biocompatible than latex (less tendency to cause allergic reactions), are odorless and tasteless, and have a longer shelf life. Further, there are no limitations on the types of lubricant which can be used with polyurethanes—they are inert, for example, to oil-based lubricants such as petroleum jelly.

The availability of polyurethanes and other high strength elastomers permits one to form sheaths of extraordinary thinness without compromising on the strength of the material or its ability to resist pinhole formation. These materials lack however a high degree of elasticity, and as a result are somewhat difficult to place over the body member for use, particularly when this is done by unrolling the sheath over the member. In the case of condoms, border rings are generally incorporated into the condom structure to facilitate the unrolling. Without such rings, the condom would be difficult to grasp and would lack the bulk needed to permit it to be unrolled. It would also have a tendency to roll back on itself.

These border rings are generally made of the same material as the condom, however, with high strength materials, considerable force is required to stretch the ring enough to position the condom as well as unroll it. This is particularly true when the circumference of the body member is larger than the diameter of the rolled condom. The result is discomfort to the user as well as a risk of tearing the condom during application. Similar problems, although less critical, are encountered during removal of the condom (as well as other types of prophylactic sheaths) after use.

SUMMARY OF THE INVENTION

It has now been discovered that thin, highstrength elastomeric polymer prophylactic sheaths can be constructed or assembled in such a manner that they can be easily rolled onto a body member prior to use, without loss of any of the advantageous properties of the sheath material. This result is achieved by augmenting the border along the open end of the sheath with a resilient material having a tensile modulus substantially lower than that of the polyurethane forming the sheath itself. It has been discovered that modifying the border for attaching a ring or collar of such material to it both facilitates the rolling of the edge and the stretching of the sheath material as it is being rolled onto the body member. Further, the sheath is securely retained during use and readily removed after use.

DETAILED DESCRIPTION OF THE INVENTION AND PREFERRED EMBODIMENTS

The term "tensile modulus" (or "modulus of elongation") preceded by a percentage is used in this specification to denote the force required to stretch the material to increase its length by the stated percentage of its original length. The modulus is commonly expressed in pounds force per square inch of the material cross section (psi). Materials typically used for condoms have a 100% tensile modulus on the order of magnitude of 100 psi (or higher). Elastomers of the type sought for use as the sheath in the present invention will have tensile moduli of at least about 200 psi.

In accordance with the present invention, the augmented border at the open end of the sheath will have a tensile modulus substantially lower than that of the sheath material. Preferred materials for the border will have a tensile modulus lower than that of the sheath by at least about 25% (i.e., the tensile modulus of the border will be 75% or less of that of the sheath material), with those lower by at least about 50% more preferred, and those lower by at least about 75% the most preferred. In terms of the actual value of the 100% tensile modulus, preferred materials are those less than 100 psi, and particularly effective results have been achieved with materials having a 100% tensile modulus of between about 10 psi and about 70 psi.

The augmented border of the present invention will have sufficient bulk to promote rolling of the sheath edge. Accordingly, the border will be substantially thicker than the material of the sheath itself. Preferred borders will have a thickness ranging from about 10 to about 300 times the thickness of the sheath material, with about 50 to about 200 times the most preferred.

The augmented border is conveniently formed as a ring (having a circular cross section) or band (having a flat profile) encircling the open end of the sheath. The ring or band may be a removable adjunct of the sheath or permanently attached to it. A permanently attached ring or band may be bonded to the sheath material, having been applied thereto while the polymer of the sheath is in the process of curing, or after curing is complete. Bonding may be achieved by the curing process itself, or by the use of adhesives, or by other conventional techniques known to those skilled in the art, such as fusing by the use of heat or solvents.

A common method of forming condoms and other prophylactic devices from elastomeric materials is by dip molding. According to this method, a form of the desired shape (which in the case of condoms will be that of a mandrel) is dipped to a preselected depth in a solution of the elastomer or elastomer-forming components, then withdrawn from the solution to retain a film over the exterior of the form, and then solidified by evaporating the solvent and/or curing the components to form the elastomer, depending on the system used. Details of these techniques are well known to those skilled in the art. The material used to form the augmented border is preferably applied to the sheath while it is still on the form, either before or after the drying and/or curing of the sheath material has been completed, depending on whether the border is intended to be permanently attached or removable. In either case, once the border is in place and the sheath is fully solidified, the border and sheath are removed together from the form in the well known manner of rolling down.

For augmented borders which are permanently attached, the border material may be applied to the sheath in a variety of ways. For example, the border material may be supplied to the form of a tape, which may be coated on one or both sides with an adhesive. Once the form has been removed from the polymer or prepolymer solution and the solidified polymer has been formed or has begun to form, the tape will be wrapped around the film along border. A small excess of tape is used to form a slight overlap at the abutting ends. The tape will also overlap the film, and may either be placed entirely below the dip line (i.e., in full contact with the film), or partially above and partially below the dip line so that a portion of the tape will contact the bare surface of the form. The tape is then rolled back over itself to form a ring of substantially circular cross section. When a tape with an adhesive coating on one side is used, the tape is positioned with the coated side facing the sheath material (i.e., inward) so that the tape will be bonded to the sheath upon application. Bonding may also be achieved by applying the tape and rolling it while the sheath material is less than fully dried or cured, and still in a tacky state. Subsequent drying (and curing if necessary) then secures the bond. As the ring is rolled, it remains in contact with the polymer film, and draws the film along with it, encircling the tape as it is being rolled. Depending on the number of revolutions and on the placement of the tape relative to the dip line, the sheath material film may be either entrapped within the ring structure (interleaved with the border material) or merely form an outer layer surrounding the ring.

The latter arrangement is conveniently achieved by first dipping the form to a dip line which is a preselected distance higher (0.25 inch, for example) than the desired length of the sheath, then using a border material tape whose width is twice this distance (e.g., 0.50 inch), and placing the midline of the tape over the dip line, the tape thereby being half on and half off the film. The tape will be of a thickness (for example, between 0.03 inch and 0.06 inch) whereby the tape is fully rolled into a ring with approximately two full revolutions and the sheath film is confined to the exterior of the ring as a casing. The resulting ring is then prevented from unrolling either by adhesive on the tape (one or both sides, both sides preferred) or the subsequent completion of the drying or curing of the sheath material (if the operation was performed while the material was still in a tacky state). It is preferred that a portion of the sheath material be rolled with the tape in forming the ring, since this detaches the edge of the sheath material from the form, aiding the ultimate removal of the entire product from the form.

An alternative method is to place the tape on the form prior to dipping the form in the solution. Preferred tape materials for this method are closed cell foam tapes or solid elastomer tapes, and a preferred procedure for this method would be to dip the form with tape attached into the solution to a depth covering about one-half the width of the tape. The form is then removed from the dipping solution and the solvent permitted to evaporate and the polymer to cure if necessary. Once this has occurred, the tape is rolled down as before to form the ring, and if this is done while the sheath material is still in a tacky state, the sheath material is permitted to cure before the entire product is rolled down off the form; otherwise, it may be rolled down immediately.

A variation on this method is the use of a large-diameter, thin-walled "lay-flat" tube to be used in place of the tape. The term "lay-flat" tube is used herein to refer to a tube which collapses upon itself (i.e., flattens) when not supported. The tube is similar to the tape, although not bearing an adhesive coating. For condom manufacture, the tube will typically have a diameter of about 1.25 to about 1.5 inches, and a wall thickness of about 0.005 inch to about 0.020 inch. In a typical procedure, a short length lay-flat tube will be placed over the form prior to dipping in the sheath prepolymer solution. The form is then dipped, immersing the short tube length entirely. Once the form is withdrawn from the dipping solution, the tube is rolled back over itself while the sheath material is still slightly wet (either due to incomplete solvent evaporation or incomplete curing or both) in order to secure the structure of the resulting ring. This embodiment will incorporate a larger portion of the sheath material in the ring, thereby limiting the difference in elastic properties between the ring and the remainder of the sheath.

The lay-flat tube may alternatively be placed on the form after the dipping process, again while the sheath material is still slightly wet. The tube is then rolled down to form the ring as before.

One method of obtaining a lay-flat tube for use in this type of procedure to manufacture condoms is by using a portion of a commercially available latex condom as the lay-flat tube. For example, a two-inch long center section cut from a Lifestyles ™ Extra-Strength latex condom (manufactured by Ansell, Doltham, Alabama) may be used. The wall thickness of this tube is approximately 0.004 inch. With the tube fully overlapping the sheath material film, the film is rolled down the form until the tube is completely encased. The resulting ring has a diameter of approximately 0.120 inch. As a further example, a one-inch tube having a thickness of 0.008 inch may be substituted for the twoinch tube.

An alternative form of the augmented border, still within the scope of the present invention, is that of a flat band encircling the sheath along the border, rather than a ring. In certain circumstances, the band will be preferable to a ring since it provides advantages in its retentive function. The constricting force will be spread over the full width of the band, providing a contact area much larger than that provided by a ring. This improves the comfort of the sheath to the user, and also permits the use of a greater amount of tension in the band as a whole without discomfort to the user.

The band may generally be formed in the same manner as the various ring methods described above, without the final rolling step. For example, border material in the form of a tape coated on one side with adhesive may be used, preferably applied to the sheath after the latter has been formed and dried tack-free, without extending above the dip line. In any event, the sheath must be completely cured and tack-free before it is rolled off the form, thereby preventing the tape from becoming permanently encased in the sheath material. The width of the tape will vary according to preference, although generally ranging from about onehalf inch to about four inches.

The ring may also be formed in place by applying the border material to the border in liquid form, either as a prepolymer resin or polymer solution. The liquid may be applied with a spreader or brush over a region of defined width along the dip line, the width being approximately one to three inches. The polymer is then solidified (by drying and/or curing) and a ring or band is formed in the same manner as described above using a tape or lay-flat tube. In preferred procedures where a ring configuration is sought, the applied liquid for the border material is confined to the area above the dip line so that it abuts or only slightly overlaps the sheath film produced by the dip. The applied liquid is then partially solidified (dried and/or cured) and the ring is formed by rolling the resulting band down over the form to the dip line.

As examples of this procedure, a reactive mixture of a polyurethane or silicone foaming resin may be used as the liquid. An example is Hypol TM polyurethane resin, available from Grace Organic Chemicals, Lexington, Massachusetts. This liquid resin foams when mixed with water, and may be applied to foam in place on the sheath form. The ultimate product is s soft, stretchy foam polyurethane. An example of a silicone resin is SWS 951 Silicone RTV, a thixotropic, room temperature vulcanizing ("RTV") silicone rubber resin available from SWS Silicones Corporation, Adrian, Michigan.

A further example is a thermoplastic elastomer such as Kraton TM D1117 styrene-isoprene-styrene block copolymer, available from Shell Chemical Co., Houston, Texas. This material may be dissolved in a suitable solvent and applied as a solution, and the solvent then evaporated in place. This material may further be applied with a dispenser known to those skilled in the art as a "hot melt" dispenser, eliminating the need for a volatile solvent.

A still further alternative within the scope of the invention is the use of a preformed ring. The preformed ring will be of a low tensile modulus material and may be in the form of an "O" ring, il.e., a circular cross section ring such as those normally used as gaskets in plumbing equipment and machinery. An example of an "O" ring of suitable properties for use in the present invention is a foam silicone elastomer "O" ring with an inside diameter of approxiamtely 1.2 inches, and a circular cross section diameter of approximately 0.125 inch. The "O" ring may be placed on the form at or near the level of the dip line, either before or after dipping in the sheath material solution. With a single roll of the sheath prior to complete drying or curing, the "O" ring becomes encased in the sheath material. "O" rings of square rather than circular cross section (commonly known as rubber bands) may also be used, but are less preferred due to their relative difficulty in facilitating the unrolling of the sheath during placement on the body member.

In a still further embodiment of the invention, a thin elastic element surrounded by fabric or other space-consuming material may be used in place of the "O" ring. Common elastic thread, for example, containing Spandex fiber surrounded by fabric may be used. The combination of materials involved in this type of construction provides the final ring with an overall tensile modulus within the range as specified for the present invention.

A still further means of permanently applying an augmented border with low tensile modulus is by the use of a composite dipping procedure. According to such a procedure, the form is dipped into prepolymer solutions in sequence, the first being a solution of low dissolved solids content, the solute being a soft elastomer, and the second being the solution used to form the sheath material. The first dip will be to a greater depth than the second, which will correspond to the length of the finished condom. The soft elastomer film will be extremely thin (0.0004 inch in thickness) but of great length (in this case, for example, 14 inches beyond the length of the sheath material film). The bare portion of the inner film once formed is rolled down the form while the film is still in the tacky state to form the ring, the rolling stopped at or close to the dip line of the outer film. The resulting product has a sheath comprised of a laminate of the two layers, terminating in a ring formed of the softer material only. Alternatively, the sheath material layer may be inside and the soft elastomer layer on the outside. Rolling is down in the same way, producing substantially the same effect.

A still further way of achieving the bulk and low tensile modulus of the ring is to incorporate a mechanical material such as a corrugated or wound-spring material into the sheath along the border. The corrugated or wound-spring material may be made from the same elastomer used as the sheath material, although formed into the appropriate configuration, the ultimate shape providing the low elastic modulus effect. Alternatively, an accordion-folded configuration may be used.

A still further means of augmenting the border with the bulk and high elasticity of a ring is to form a border structure which incorporates trapped air, water or some other liquid, or a gel in the central lumen of the ring. The selection of the fluid and the appropriate combination of the fluid and the solid material in the ring will be selected to produce a ring having an elastic modulus within the desired range. As one example, a silicone tube having an outside diameter of approximately 0.125 inch and a wall thickness of approximately 0.030 inch, formed into an "O" ring, may be rolled inside the sheath material to produce a border ring of suitable characteristics.

As stated above, the present invention also extends to removable rings or bands, which are useful in cases where they are needed to facilitate the rolling of the edge and the stretching of the sheath as it is being placed over the body member, but not to retain the sheath in place during use. Certain condoms, for instance, are coated with a nontoxic biocompatible adhesive to hold them in place. In such cases, once the condom has been unrolled and fully positioned over the member, the ring is no longer needed as a retaining element and may be removed separately, leaving the condom in place.

Many of the methods described above may be adapted to form removable rings or bands, generally by permitting the sheath to fully solidify (dry and/or cure) before applying the preformed ring or band to the region of the dip line, using any of the various materials mentioned. One example is the use of a flat piece of styrene-isoprene-styrene block copolymer commercially available from Shell Chemical Co., Houston, Texas, by the product name Krayton D1117. A strip of this material measuring 0.5 inch in width, 0.030 inch in thickness and 4.5 inches in length is interrolled with the open end of the completely dried and cured condom as the condom is stripped from the mandrel. Other suitable materials similar to those described above will be readily apparent to those skilled in the art. The removable ring or band will typically be encased in the rolled-up condom, used to advantage to facilitate the unrolling of the condom as it is being placed over the body member, and then removed once the condom is fully in place.

The augmented border, whether it be a ring or a band may be made from any of a wide range of materials meeting the requirement of having a low 100% tensile modulus. Examples of these materials are certain polyurethanes, plasticised polyurethanes, latex rubbers, silicone elastomers, ethylene-propylene thermoplastic elastomers and styrene block copolymer thermoplastic elastomers such as styrene-butadiene-styrene block copolymers, styrene-isoprene-styrene block copolymers, and styrene-isoprene multiarm (branched) copolymers. Further examples are olefinic thermoplastic elastomers, polyether-block-amide thermoplastic elastomers, polyvinylchlorides and acrylic-based thermoplastic elastomers. The ring or band may also be in the form of a hot-melt or pressure-sensitive adhesive. Foam polymers such as foam polyurethanes and foam silicone elastomers are preferred. The most preferred are foam polyurethanes. Specific examples within several of these categories appear throughout the description above.

As stated above, the present invention is applicable to sheaths fabricated from a variety of materials. The chemical identity of the sheath material is not critical, and sheaths of a wide range of such materials will benefit from the present invention. Sheath materials of greatest interest are those having high strength, low hardness, and a high tensile modulus, particularly a 100% tensile modulus of at least about 200 psi. Preferred materials are those having a tensile strength of at least about 6000 psi, a Shore A hardness of about 50 to about 90, and a strength to hardness ratio (in these units) of about 50 to about 200, with about 80 to about 150 particularly preferred.

One example of a class of sheath materials meeting these criteria is that of thermoplastic elastomers in the form of block copolymers. As is known among those skilled in the art, these copolymers are formed of hard and soft segments—the soft segment generally comprising a long chain flexible component having a glass transition temperature below room temperature, and the hard segment comprising a shorter stiffer component having a glass transition temperature above room temperature and tending toward physical cross linking with like segments. A wide variety of block copolymers meeting this description may be used. One example is a product designated T722-A, available from E. I. du Pont de Nemours & Co., Inc., Wilmington, Delaware, identified by the manufacturer as a polyether copolymer with polyether soft segment. Sheaths made of this material are preferably formed by dipping the form in a solution or liquid mixture of the polymer-forming components and heat curing the components on the form after withdrawal to form the copolymer. Alternatively, the sheath may be formed by dipping the form in a solution of the copolymer in a volatile solvent, followed by withdrawal of the form to leave a film of the solution on the form surface, then evaporating the solvent from the film. A wide range of solvents may be used. A preferred solvent is meta-cresol.

Another class of sheath materials meeting the above criteria are polyurethanes. Preferred polyurethanes are those which are soluble in a volatile solvent at high concentrations, permitting one to form a film of the solution over the sheath form (by dipping the sheath in the solution and withdrawing it) and evaporating the solvent to leave a finished product without the need for further curing. Thermoplastic, primarily linear polyurethanes are preferred. Examples include both polyether-based and polyester-based polyurethanes, as well as those based on a combination of both. Examples further include polyurethanes in the form of block copolymers, and polyurethanes containing chain extenders and modifers.

The polyurethanes may be formed from a wide range of polyisocyanates and polyols. Examples of polyisocyanates are aromatic and alicyclic diisocyanates such as 4,4'-diphenyl methane diisocyanate (MDI), toluene diisocyanate (TDI), isophorone diisocyanate (IPDI), methylene bis-(4-cyclohexyl) diisocyanate (HMDI), and 1,4-diisocyanatobenzene (PPDI). Examples of polyester diols are polylactones such as polycaprolactone polyol, and copolymers of short chain diols and aliphatic dicarboxylic acids such as poly(ethylene adipate) polyol, poly(ethylene succinate) polyol, poly(ethylene sebacate) polyol, poly(butylene adipate) polyol, and poly(diethylene ether adipate) polyol. An example of a polyether polyol is poly(tetramethylene ether) glycol. All such materials are well known among those skilled in the art, and either commercially available or capable of preparation by conventional methods. Many such materials and the polymers formed from them are commercially available.

A wide range of solvents may be used, providing that they are inert with respect to the particular polyurethane used, stable throughout the conditions encountered during formation of the sheath, and preferably volatile and capable of dissolving the polyurethane in high concentrations. Examples are aliphatic hydrocarbons, such as for example n-pentane, n-hexane, and isohexane; alicyclic hydrocarbons, such as for example cyclopentane and cyclohexane; aromatic hydrocarbons, such as for example benzene and toluene; halogenated hydrocarbons, such as for example methylene dichloride, 1,2-dichloroethane, 1,1,1-trichloroethane, and 1,1,2-trichloroethane; esters, such as for example ethyl acetate; ethers, such as for example diethyl ether, ethyl n-propyl ether, and ethyl isopropyl ether; ketones, such as for example acetone and methyl ethyl ketone; and heterocyclic compounds, such as for example furan, tetrahydrofuran, and alkyl- and halo-substituted analogs of these.

The polyurethane used for the sheath will be one which combines high strength with a high degree of softness. The strength, expressed in terms of tensile strength, will be at least about 6,000 psi, preferably from about 6,000 to about 10,000 psi, and most preferably from about 7,000 to about 9,000 psi. The softness, expressed as Shore A hardness, preferably ranges from about 50 to about 90, most preferably from about 60 to about 80. With these properties, the thickness of the sheath is selected to produce the desired ultimate strength and 100% tensile modulus. The thickness is generally less than about 0.0014 inch, and preferably ranges from about 0.0004 inch to about 0.0014 inch, most preferably from about 0.0006 inch to about 0.0008 inch. Likewise, the 100% tensile modulus will be at least about 200 psi, preferably from about 300 psi to about 600 psi. The strength to hardness ratio, expressed in terms of the units given above, will generally range from about 50 to about 200, preferably from about 80 to about 150.

One example of a sheath material is Q-Thane Thermoplastic Elastomer PS49-100, a product of K. J. Quinn and Co., Inc., Malden, Massachusetts, a thermoplastic polyester urethane having a Shore A hardness of 70–75, a specific gravity of 1.15, a tensile strength of 8000 psi, a 100% modulus of elongation of 550 psi, a 300% modulus of elongation of 1650 psi, an elongation of 560%, and a tear strength of 400 psi. A particularly effective solution of this polyurethane is a tetrahydrofuran solution at between 14% and 18% by weight of the solute, having a viscosity within the range of about 400 to about 1500 centipoise.

The foregoing is offered primarily for purposes of illustration. It will be readily apparent to those skilled in the art that numerous modifications and variations of the components, dimensions and parameters described above may be made without departing from the spirit and scope of the invention.

What is claimed is:

1. A prophylactic device comprising a sheath of elastomeric sheet material having a 100% tensile modulus of at least about 200 psi and a thickness of less than about 0.0014 inch, said sheath having an open end and with a border containing a resilient material having a 100% tensile modulus substantially lower than that of said elastomeric sheet material, said resilient material being a member selected from the group consisting of polyurethanes, latex rubbers, silicone elastomers, foam silicone elastomers, ethylenepropylene thermoplastic elastomers, styrenic block thermoplastic elastomers, olefinic thermoplastic elastomers, polyether-block-amide thermoplastic elastomers, plasticized polyvinylchlorides, and acrylic-based thermoplastic elastomers, and the ratio of the thickness of said border to the thickness of said sheath being from about 10 to about 300.

2. A prophylactic device in accordance with claim 1 in which the 100% tensile modulus of said resilient material is lower than that of said elastomeric sheet material by at least about 25%.

3. A prophylactic device in accordance with claim 1 in which the 100% tensile modulus of said resilient material is lower than that of said elastomeric sheet material by at least about 50%.

4. A prophylactic device in accordance with claim 1 in which the 100% tensile modulus of said resilient material is lower than that of said elastomeric sheet material by at least about 75%.

5. A prophylactic device in accordance with claim 1 in which said elastomeric sheet material has a thickness of less than 0.0014 inch, a tensile strength of at least about 6000 psi, and a ratio of tensile strength to Shore A hardness of from about 50 to about 200, and the 100% tensile modulus of said resilient material is less than about 100 psi.

6. A prophylactic device in accordance with claim 1 in which said elastomeric sheet material is a polyurethane.

7. A prophylactic device in accordance with claim 1 in which said elastomeric sheet material is a polyurethane and has a thickness of about 0.0004 inch to about 0.0014 inch, a tensile strength of about 6000 psi to about 10000 psi, and a 100% tensile modulus of about 300 psi to about 600 psi, and the 100% tensile modulus of said resilient material is less than about 100 psi.

8. A prophylactic device in accordance with claim 1 in which said elastomeric sheet is a polyurethane and has a thickness of about 0.0006 inch to about 0.0008 inch, a tensile strength of about 7000 psi to about 9000 psi, and a 100% tensile modulus of about 300 psi to about 600 psi, and the 100% tensile modulus of said resilient material is from about 10 psi to about 70 psi.

9. A prophylactic device in accordance with claim 1 in which said border is comprised of said resilient material encased in a layer of material identical to said elastomeric sheet material.

10. A prophylactic device in accordance with claim 9 in which said resilient material is a ring of substantially circular cross section.

11. A prophylactic device in accordance with claim 9 in which said resilient material is a substantially flat band rolled back over itself.

12. A prophylactic device in accordance with claim 11 in which said flat band is coated on one side with adhesive.

13. A prophylactic device in accordance with claim 11 in which said flat band is coated on both sides with adhesive.

14. A prophylactic device in accordance with claim 1 in which said border is comprised of a substantially flat band of said resilient material.

15. A prophylactic device in accordance with claim 1 in which said resilient material includes a member selected from the group consisting of styrene-butadienestyrene block copolymer, styrene-isoprenestyrene block copolymer, and styrene-isoprene-multiarm (branched) copolymer.

16. A prophylactic device in accordance with claim 1 in which said resilient material includes styrene-isoprene-styrene block copolymer.

17. A prophylactic device in accordance with claim 1 in which said resilient material includes styrene-isoprene-styrene block copolymer in the form of a member selected from the group consisting of a hot-melt or pressure-sensitive adhesive.

18. A prophylactic device in accordance with claim 1 in which said resilient material is a foam polymer.

19. A prophylactic device in accordance with claim 1 in which said resilient material is a foam polyurethane.

20. A prophylactic device in accordance with claim 1 in which the ratio of the thickness of said border to the thickness of said sheath is from about 50 to about 200.

21. A prophylactic device comprising a polyurethane sheath having a thickness of about 0.0006 to about 0.0008 inch, a tensile strength of about 7000 psi to about 9000 psi, and a 100% tensile modulus of at least about 300 psi, said polyurethane sheath having an open end with a border containing a ring of foam polyurethane having a 100% tensile modulus of about 10 psi to about 70 psi, the ratio of the thickness of said border to the thickness of said sheath being from about 10 to about 300.

22. A prophylactic device in accordance with claim 1 in which said resilient material is bonded to said border.

23. A prophylactic device in accordance with claim 1 in which said resilient material is a ring not bonded to said sheath.

* * * * *